United States Patent [19]

Telschow

[11] Patent Number: 4,614,814

[45] Date of Patent: Sep. 30, 1986

[54] MONOALKYLATION OF DIHYDROXY AROMATIC COMPOUNDS

[75] Inventor: Jeffrey E. Telschow, Tarrytown, N.Y.

[73] Assignee: Stauffer Chemical Company, Westport, Conn.

[21] Appl. No.: 724,363

[22] Filed: Apr. 17, 1985

[51] Int. Cl.[4] ............................................. C07C 69/76
[52] U.S. Cl. ....................................... 560/61; 560/78; 568/753
[58] Field of Search ..................... 560/61, 78; 568/753, 568/766

[56] References Cited

FOREIGN PATENT DOCUMENTS 1591063 6/1981 United Kingdom .................. 560/61

OTHER PUBLICATIONS

Newman et al., "J. Organic Chemistry", vol. 39 (1950) pp. 214–215.
Moser "J. American Chemical Society", vol. 72 (1950) pp. 1413–1415.

Primary Examiner—Werren B. Lone

[57] ABSTRACT

There is disclosed a process for the reduction of the diether impurities formed when a dihydroxy aromatic compound is reacted with an alkylating agent in an alcoholic solvent in the presence of two to three equivalents of base. The diether impurities are removed by removing a quantity of the alcoholic solvent and adding a solvent into which the diether impurities may be extracted.

6 Claims, No Drawings

MONOALKYLATION OF DIHYDROXY AROMATIC COMPOUNDS

FIELD OF THE INVENTION

The present invention relates to an improved process for the monoalkylation of dihydroxy aromatic compounds.

BACKGROUND OF THE INVENTION

The selective monoalkylation of dihydroxy aromatic compounds, for example, hydroquinone, presents problems because both hydroxy groups tend to react with the alkylating agent. Newman and Colla (Journal of Organic Chemistry, Vol. 39, pages 214 and 215 (1974)) state that the monoalkylation of hydroquinone represents a problem for which no generally satisfactory procedure has as yet been developed. Monoalkylation has been accomplished by using a large excess of hydroquinone, but this method is not efficient if yield is calculated on hydroquinone. In general, alkylation of hydroquinone via the monosodium salt and one equivalent of the alkylating agent gives poor yields of monoalkylated product. Alternatively, one can make a monoprotected hydroquinone, itself a difficult process, alkylate, and remove the protecting group. These workers found that aqueous dioxan gave good yields of monoalkylation product when alkali-stable alkylating agents are used, for example, tert-butyl bromoacetate, the tert-butyl group of which is not hydrolyzed off by alkali. Similarly N-methylpyrrolidone/water also gave a good yield of monoalkylated product using tert-butyl bromoacetate. However, when alkali-sensitive groups are present as in ethyl alphabromoisobutyrate, these solvent systems are ineffective. Only moderate yields of monoalkylation product are obtained with this alkylating agent using dimethylformamide or dimethylsulphoxide as solvents.

A paper by Moser (Journal of the American Chemical Society, Vol. 72, pages 1413–1415 (1950)) discloses that reaction of the disodium salt of hydroquinone with one equivalent of ethyl chloroacetate gave approximately 30% of monoalkylation product (7% of acid; 23% of ethyl ester).

In the United Kingdom Pat. No. 1,591,063, a dihydroxybenzene compound, particularly hydroquinone, is monoalkylated in an alcoholic solvent using two to three equivalents of a base. While the above process may result in commercially acceptable yields of the desired product, the purity of the final product is not suitable for many applications. In particular, the above process does not indicate any procedure for the removal of dialkylated reaction products. Minimizing these diether by-products is mandated when the final product needs to be substantially pure.

SUMMARY OF THE INVENTION

In accordance with the present invention, there is disclosed a process for the removal of diether impurities formed when a dihydroxy aromatic compound is alkylated in an alcoholic solvent in the presence of two to three equivalents of base. The diether impurities are removed by removing a quantity of the alcoholic solvent and replacing said removed quantity with a solvent into which said diether impurities can be extracted.

DETAILED DESCRIPTION OF THE INVENTION

The present invention is directed to a process for the removal of diether impurities formed during the formation of a monoalkylated dihydroxy aromatic compound of the formula

wherein Y is an aromatic compound of up to three fused rings, said aromatic compound optionally substituted by halogen, alkoxy or alkyl groups or Y is a heterocyclic aromatic compound said heterocyclic aromatic compound being optionally substituted by halogen, alkoxy or alkyl groups, A is an optionally substituted straight chain or branched chain alkyl group of from 1 to about 20 carbon atoms in which the chain may be interrupted by oxygen or sulfur atoms or an aralkylene radical or an alkenylene group, and Z is an electron withdrawing group.

Said dihydroxy aromatic compounds may be formed by any number of methods with one preferred mode of formation being the reaction of a compound of the formula

wherein Y is as defined above with an alkylating agent of the formula

wherein W is a halogen atom, and A and Z have the meanings defined above, in an alcoholic solvent and in the presence of two to three equivalents of a base. The above reaction may be summarized as follow:

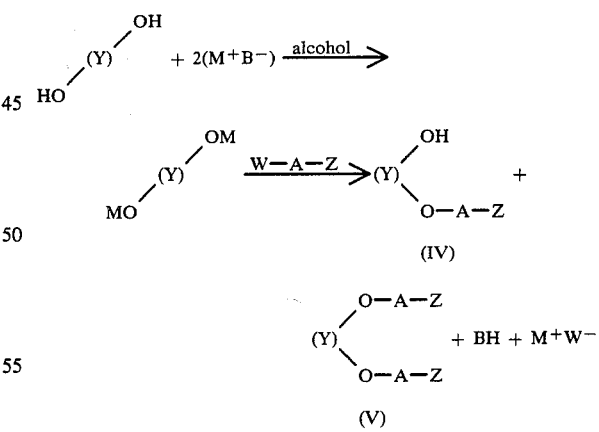

in which Y, W, A and Z are as previously defined, M+ is an alkali metal or alkaline earth metal cation and B− is a basic function such as methoxide, ethoxide or hydride. It can be seen that product IV, in addition to containing the desired monoalkylated, hydroxy aromatic compound, also contains product V, the diether impurity. It has now been surprisingly found that the quantity of the diether impurity in the final product can be reduced, hence increasing the monoether/diether ratio, by distilling a quantity of the alcoholic solvent and treating the resulting concentrated salt solution or suspension with a quantity of a solvent into which the diether impurity may be extracted.

In the present invention, examples of groups represented by A include straight or branched chain alkyl groups of 1-20 carbon atoms with examples of each alkyl groups being ethyl, methyl, propyl and the like.

Examples of electron withdrawing groups represented by A are —COOR, —CN and CONRR' in which R and R' each independently represent a hydrogen atom or an optionallysubstituted hydrocarbon radical or R and R' together may form a heterocyclic ring including the amide nitrogen atom. When R and R' are hydrocarbon radicals, it is preferred that they are alkyl radicals and further preferred that they are lower alkyl radicals. Exemplary groups represented by Z are methoxycarbonyl, ethoxycarbonyl and aminocarbonyl.

When the group B represents an alkoxy group, it is preferred that this is a lower alkoxy group of 1-4 carbon atoms. B can also be a hydrogen atom. Examples of alkoxy groups represented by B are methoxy and ethoxy.

Examples of halogen atoms represented by W include chlorine, bromine, iodine and fluorine. Y may also contain any of the above halogens.

Alcoholic solvents which may be used in the process of the current invention include ethanol and methanol.

Examples of bases which may be used include sodium methoxide, sodium ethoxide, potassium methoxide, potassium ethoxide, sodium hydride, potassium hydride and the like.

Dihydroxy aromatic compounds which may be used as starting materials include hydroquinone, chlorohydroquinone, resorcinol, fused ring dihydroxy aromatic compounds such as dihydroxynaphthalene, dihydroxyanthracene and heterocyclic aromatic compounds such as dihydroxypyridine, dihydroxyfuran, and dihyroxythiophene.

Suitable alkylating agents represented by the formula W—A—Z include methyl chloroacetate, ethyl chloroacetate, ethyl alphachloropionate and methyl alphachloropionate.

Suitable solvents into which the diether impurity may be extracted include aromatic solvents such as toluene, xylene, hexane, trichloroethylene, tetrachloroethylene, carbon tetrachloride or other non-polar aprotic inert solvents. The solvent is chosen based on the fact that a two phase mixture is formed when the original alcoholic solvent is concentrated upon distillation of said alcoholic solvent.

The reaction may be carried out at normal room temperature or at elevated temperatures for a reaction period of, for example, from about 2 to about 24 hours depending on temperature. The temperatures at which the reaction is carried out is preferably that of the refluxing solvent. The reaction is also carried out under atmospheric pressure although pressures ranging from about 1 to about 50 atmospheres may be used.

A particularly suitable means for removing part of the alcoholic solvent is by distilling the alcoholic solvent.

Once the extraction step is complete, the desired product can be purified by conventional filtering, washing and crystallization techniques. An additional solvent extraction step can also be added.

The present process enables good yields, i.e. up to 70 percent or even higher, of monoalkylation products of hydroquinone or other dihydroxy aromatic compounds.

The present process also enables yields of high purity product. By removing a portion of the alcoholic solvent and replacing some or all of the removed portion with a solvent into which the diether impurity may be extracted, products of a purity ranging from about 90 percent to about 99 percent, by weight, are obtained. Also monoether/diether ratios ranging from about 20 to about 200 are also obtained.

The monoalkylated dihydroxy aromatic compounds obtained according to the present invention are of value as intermediates in the synthesis of dyestuffs. For example, by following the procedures of United Kingdom Pat. No. 1,591,063, said procedures being incorporated herein by reference, an anthraquinone dyestuff of the formula:

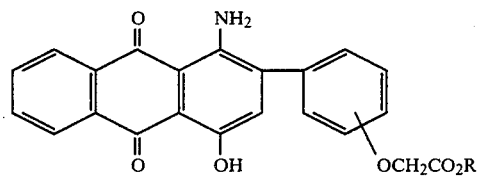

wherein R is an alkyl group, may be obtained.

The present invention is illustrated by the following examples.

COMPARISON EXAMPLE 1

The following example shows the effect of essentially following the procedures of United Kingdom Pat. No. 1,591,063 with th substitution of methyl chloropropionate for ethyl chloropropionate to produce methyl 2-(4-hydroxyphenoxy)-propionate (MHPP).

To a 1 liter 3-necked round bottomed flask under nitrogen was added 139 milliliters of methanol. The reaction vessel was placed in a water bath and over a period of 10 minutes, a total of 4.6 grams (0.20 moles) of sodium was added. After the sodium had been added, the reaction mixture was stirred for 15 minutes under nitrogen and then 11.0 grams (0.10 mole) of hydroquinone was added. 12.3 grams (0.10 mole) of methyl chloropropionate was then added to the reaction vessel and the mixture was heated to reflux. At the completion of the reaction (12 hours), 6.0 grams (0.1 mole) of acetic acid was added, the methanol was stripped on a rotary evaporator, 139 milliliters of methylene chloride was added and the mixture was extracted with water. Evaporation of methylene chloride gave 14.3 grams of beige crystals (73 percent crude yield). Gas chromatographic analysis of the final product showed the following:

| | |
|---|---|
| Purity (weight percent) | 79.6 |
| Mono/diether ratio | 6.5 |

EXAMPLE 1

The following example shows the effect of following the procedure of Comparison Example 1 with the addition of the steps of removing a portion of the alcoholic solvent followed by replacement of the removed solvent with toluene and decanting the toluene containing the diether impurity.

To a 500 ml, 3-necked round bottom flask equipped with a Vigreaux column, dropping funnel and nitrogen inlet was added 123 milliliters of methanol under nitrogen. To the methanol was then added 6.9 grams (0.3 mole) of sodium. After all the sodium had been added, 16.5 grams (0.15 mole) of hydroquinone was added, the mixture was heated to reflux, and then 11.4 milliliters (0.10 mole) of methyl chloropropionate was added dropwise over 45 minutes. The mixture continued to reflux for 3 hours, and then methanol was allowed to distill. After approximately 125 milliliters of methanol had been collected, a total of 100 milliliters of toluene was added to the reaction vessel.

The mixture was allowed to cool and the toluene layer was removed with a syringe. The mixture was then extracted with another 30 milliliters of toluene. The product salt paste was then diluted with another 100 milliliters of toluene and neutralized with 12 grams of acetic acid. A total of 100 milliliters of cold water was then added. The remaining product was then purified using countercurrent extraction with another 50 milliliters of toluene. 14.3 grams of light brown crystals with a melting point of 50°–57° C. were obtained. The crude yield was 73.0 percent and purity by gas chromatography assay was 94.3 weight percent.

EXAMPLE 2

The following table shows the comparison between the products produced with and without the toluene extraction step.

TABLE I

| Product | Product Comparison | | Mono/diether Ratio (m/d) |
|---|---|---|---|
| | Crude Yield (%) | Purity (wt. %) | |
| MHPP (Comparison Ex. 1) | 73.0 | 79.6 | 6.5 |
| MHPP (Example 1) | 73.0 | 94.3 | 65.5* |

*m/d = 9.4 before toluene extraction of diether.

EXAMPLE 3

Similar to Example 1 except the diether impurity was extracted into tetrachloroethylene.

Additional features of the preferred and most preferred features of the present invention are found in the claims hereinafter.

What is claimed is:

1. A process for the reduction of the diether impurities formed when a dihydroxy aromatic compound is reacted with an alkylating agent in an alcoholic solvent inthe presence of two to three equivalents of base, $M^+B^-$, wherein $M^+$ is an alkali metal or alkaline earth metal cation and $B^-$ is a basic function selected from the group consisting of methoxide, ethoxide or hydride; wherein the dihydroxy aromatic compound has the formula:

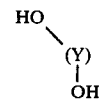

wherein Y is an aromatic compound of up to three fused rings or Y is a heterocyclic aromatic compound, said aromatic or heteroaromatic compounds optionally substituted by halogen, alkoxy or alkyl, and the alkylating agent has the formula:

wherein W is a halogen atom, A is an optionally substituted straight chain or branched chain alkyl group of from 1 to about 20 carbon atoms in which the chain may be interrupted by oxygen or sulfur or A is an aralkylene radical or an alkenylene group, and Z is an electron withdrawing group; which process comprises removing by distillation a quantity of alcoholic solvent, then adding to the reaction product an aprotic solvent capable of forming a two-phase system with the alcoholic solvent to extract into the aprotic solvent the diether impurity and yield a product with a monoether/diether ratio from about 20 to about 200.

2. The process of claim 1 wherein said alcoholic solvent is methanol.

3. The process of claim 1 wherein said removal of the alcoholic solvent is accomplished by distilling.

4. The process of claim 1 wherein said solvent is toluene.

5. The process of claim 1 wherein said solvent is tetrachloroethylene.

6. The process of claim 1 wherein the product formed is methyl 2-(4-hydroxyphenoxy) propionate.

* * * * *

UNITED STATES PATENT AND TRADEMARK OFFICE
CERTIFICATE OF CORRECTION

PATENT NO. : 4,614,814
DATED : September 30, 1986
INVENTOR(S) : Jeffrey E. Telschow It is certified that error appears in the above-identified patent and that said Letters Patent are hereby corrected as shown below:

Col. 3, line 6, "each" should be --said--;

Col. 3, line 11, "optionallysubstituted" should be --optionally-substituted--;

Col. 4, line 34, "th" should be --the--;

Col. 4, line 41, "After the" should be --After all the--;

Col. 6, line 5, "solvent inthe presence" should be --solvent in the presence--.

Signed and Sealed this

Tenth Day of March, 1987

*Attest:*

DONALD J. QUIGG

*Attesting Officer*  *Commissioner of Patents and Trademarks*